(12) United States Patent
Gasparini et al.

(10) Patent No.: US 7,348,353 B2
(45) Date of Patent: Mar. 25, 2008

(54) ACETYLENE DERIVATIVES HAVING MGLUR 5 ANTAGONISTIC ACTIVITY

(75) Inventors: Fabrizio Gasparini, Lausen (CH); Yves Auberson, Allschwil (CH); Silvio Ofner, Muenchenstein (CH)

(73) Assignee: Novartis AG, Basel (CH)

( * ) Notice: Subject to any disclaimer, the term of this patent is extended or adjusted under 35 U.S.C. 154(b) by 113 days.

(21) Appl. No.: 10/497,363

(22) PCT Filed: Dec. 3, 2002

(86) PCT No.: PCT/EP02/13670

§ 371 (c)(1),
(2), (4) Date: Oct. 26, 2004

(87) PCT Pub. No.: WO03/047581

PCT Pub. Date: Jun. 12, 2003

(65) Prior Publication Data

US 2005/0065191 A1   Mar. 24, 2005

(30) Foreign Application Priority Data

Dec. 4, 2001   (GB)   .................. 0128996.6

(51) Int. Cl.
*A61K 31/405*   (2006.01)
*C07D 209/18*   (2006.01)
(52) U.S. Cl. .............. 514/419; 514/601; 514/613; 548/495; 564/80; 564/123
(58) Field of Classification Search ........ 514/419, 514/438, 601, 613; 548/495; 564/80, 123
See application file for complete search history.

(56) References Cited

U.S. PATENT DOCUMENTS 4,129,658 A   12/1978   Berthold 5,516,904 A   5/1996   Chandraratna
6,313,071 B1   11/2001   Ikegaya et al.

FOREIGN PATENT DOCUMENTS

| EP | 0849256 | 8/1996 |
|---|---|---|
| WO | WO 97 08133 | 8/1995 |
| WO | WO 96 10012 | 9/1995 |
| WO | WO 97 48697 | 6/1997 |
| WO | WO 99 02497 | 1/1999 |
| WO | WO 99 62869 | 6/1999 |
| WO | WO 0234711 | 5/2002 |
| WO | WO 02 46166 | 6/2002 |
| WO | WO 02 062323 | 8/2002 |

*Primary Examiner*—Zinna N. Davis
(74) *Attorney, Agent, or Firm*—Cozette M. McAvoy; Peter J. Waibel

(57) ABSTRACT

The invention provides compounds of formula (I) wherein m, n, A, R, R', R", $R_0$, X and Y are as defined in the description, and their preparation. The compounds of formula (I) are useful as pharmaceuticals in the treatment of e.g. nervous system disorders

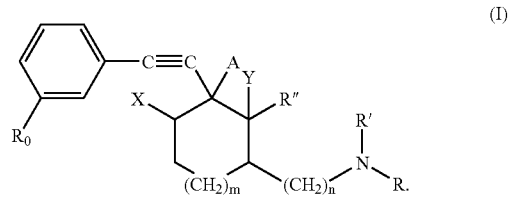

6 Claims, No Drawings

ACETYLENE DERIVATIVES HAVING MGLUR 5 ANTAGONISTIC ACTIVITY

The present invention relates to novel acetylene derivatives, their preparation, their use as pharmaceuticals and pharmaceutical compositions containing them.

More particularly the invention provides a compound of formula I

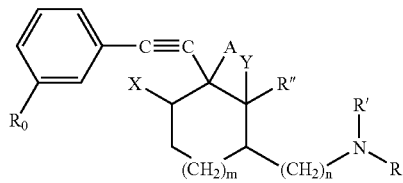

wherein
m is 0 or 1,
n is 0 or 1 and
A is hydroxy
X is hydrogen and
Y is hydrogen, or
A forms a single bond with X or with Y;
$R_0$ is hydrogen, $(C_{1-4})$alkyl, $(C_{1-4})$alkoxy, trifluoromethyl, halogen, cyano, nitro, —$COOR_1$ wherein $R_1$ is $(C_{1-4})$alkyl or —$COR_2$ wherein $R_2$ is hydrogen or $(C_{1-4})$alkyl, and
R is —$COR_3$, —$COOR_3$, —$CONR_4R_5$ or —$SO_2R_6$, wherein $R_3$ is $(C_{1-4})$alkyl, $(C_{3-7})$cycloalkyl or optionally substituted phenyl, 2-pyridyl or 2-thienyl, $R_4$ and $R_5$, independently, are hydrogen or $(C_{1-4})$alkyl and $R_6$ is $(C_{1-4})$alkyl, $(C_{3-7})$cycloalkyl or optionally substituted phenyl,
R' is hydrogen or $(C_{1-4})$alkyl and
R" is hydrogen or $(C_{1-4})$alkyl, or
R' and R" together form a group —$CH_2$—$(CH_2)_p$— wherein p is 0, 1 or 2, in which case one of n and p is different from 0,
with the proviso that $R_0$ is different from hydrogen, trifluoromethyl and methoxy when m is 1, n is 0, A is hydroxy, X and Y are both hydrogen, R is COOEt and R' and R" together form a group —$(CH_2)_2$—,
in free base or acid addition salt form.

On account of the asymmetrical carbon atoms present in the compounds of formula I and their salts, the compounds may exist in optically active form or in form of mixtures of optical isomers, e.g. in form of racemic mixtures. All optical isomers and their mixtures including the racemic mixtures are part of the present invention.

In a further aspect, the invention provides a process for the production of the compounds of formula I and their salts, which comprises the step of
a) for the production of a compound of formula I wherein A is hydroxy, reacting a compound of formula II

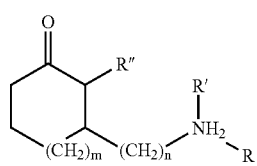

wherein m, n, R, R' and R" are as defined above, with a compound of formula III

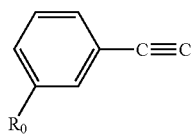

wherein $R_0$ is as defined above, or
b) for the production of a compound of formula I wherein A forms a single bond with X or with Y, dehydrating a compound of formula I wherein A is hydroxy, and recovering the resulting compound of formula I in free base or acid addition salt form.

The reaction of process a) can be effected according to conventional methods, e.g. as described in Examples I (step e), 2 (step d), 5 (step b) and 8.

The dehydratation of process b) leads to a mixture of a compound of formula I wherein A forms a single bond with X and a compound of formula I wherein A forms a single bond with Y, which are subsequently separated according to conventional methods, e.g. as described in Examples 6, 9 and 10.

A so obtained compound of formula I can be converted into another compound of formula I according to conventional methods, e.g. as described in Examples I (steps f and g), 4 and 7.

Working up the reaction mixtures according to the above processes and purification of the compounds thus obtained may be carried out in accordance to known procedures.

Acid addition salts may be produced from the free bases in known manner, and vice versa.

Compounds of formula I in optically pure form can be obtained from the corresponding racemates according to well-known procedures. Alternatively, optically pure starting materials can be used.

The starting materials of formulae II and III are known or may be obtained from known compounds, using conventional procedures.

Compounds of formula I obtained in accordance with the above-described process can be converted into other compounds of formula I in customary manner.

Resulting acid addition salts can be converted into other acid addition salts or into the free bases in a manner known per se.

The compounds of formula I, including their acid addition salts, may also be obtained in the form of hydrates or may include the solvent used for crystallization.

Compounds of formula I and their pharmaceutically acceptable acid addition salts, hereinafter referred to as agents of the invention, exhibit valuable pharmacological properties and are therefore useful as pharmaceuticals.

In particular, the agents of the invention exhibit a marked and selective modulating, especially antagonistic, action at human metabotropic glutamate receptors (mGluRs). This can be determined in vitro for example at recombinant human metabotropic glutamate receptors, especially PLC-coupled subtypes thereof such as mGluR5, using different procedures like, for example, measurement of the inhibition of the agonist induced elevation of intracellular $Ca^{2+}$ concentration in accordance with L. P. Daggett et al., Neuropharm. Vol. 34, pages 871-886 (1995), P. J. Flor et al., J. Neurochem. Vol. 67, pages 58-63 (1996) or by determination to what extent the agonist induced elevation of the inositol phosphate turnover is inhibited as described by T. Knoepfel et al., Eur. J. Pharmacol. Vol. 288, pages 389-392 (1994), L. P. Daggett et al., Neuropharm. Vol. 67, pages 58-63 (1996) and references cited therein. Isolation and expression of human mGluR subtypes are described in U.S. Pat. No. 5,521,297. Selected agents of the invention show $IC_{50}$ values for the inhibition of the quisqualate-induced inositol phosphate turnover, measured in recombinant cells expressing hmGluR5a of about 1 nM to about 50 μM.

The agents of the invention are therefore useful in the treatment of disorders associated with irregularities of the glutamatergic signal transmission, and of nervous system disorders mediated full or in part by mGluR5.

Disorders associated with irregularities of the glutamatergic signal transmission are for example epilepsy, cerebral ischemias, especially acute ischemias, ischemic diseases of the eye, muscle spasms such as local or general spasticity and, in particular, convulsions or pain.

Nervous system disorders mediated full or in part by mGluR5 are for example acute, traumatic and chronic degenerative processes of the nervous system, such as Parkinson's disease, senile dementia, Alzheimer's disease, Huntington's chorea, amyotrophic lateral sclerosis and multiple sclerosis, psychiatric diseases such as schizophrenia and anxiety, depression, pain, itch and drug abuse, e.g. alcohol and nicotine abuse and cocaine use disorders.

The usefulness of the agents of the invention in the treatment of the above-mentioned disorders can be confirmed in a range of standard tests including those indicated below:

Activity of the agents of the invention in anxiety can be demonstrated in standard models such as the stress-induced hyperthermia in mice [cf. A. Lecci et al., Psychopharmacol. 101, 255-261]. At doses of about 0.1 to about 30 mg/kg p.o., the agents of the invention reverse the stress-induced hyperthermia.

At doses of about 4 to about 50 mg/kg p.o., the agents of the invention show reversal of Freund complete adjuvant (FCA) induced hyperalgesia [cf. J. Donnerer et al., Neuroscience 49, 693-698 (1992) and C. J. Woolf, Neuroscience 62, 327-331 (1994)].

For all the above mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.5 to about 100 mg/kg animal body weight. In larger mammals, for example humans, an indicated daily dosage is in the range from about 5 to 1500 mg, preferably about 10 to about 1000 mg of the compound conveniently administered in divided doses up to 4 times a day or in sustained release form.

In accordance with the foregoing, the present invention also provides an agent of the invention for use as a pharmaceutical, e.g. in the treatment of disorders associated with irregularities of the glutamatergic signal transmission, and of nervous system disorders mediated full or in part by mGluR5.

The invention also provides the use of an agent of the invention, in the treatment of disorders associated with irregularities of the glutamatergic signal transmission, and of nervous system disorders mediated full or in part by mGluR5.

Furthermore the invention provides the use of an agent of the invention for the manufacture of a pharmaceutical composition designed for the treatment of disorders associated with irregularities of the glutamatergic signal transmission, and of nervous system disorders mediated full or in part by mGluR5.

In a further aspect the invention relates to a method of treating disorders mediated full or in part by mGluR5, which method comprises administering to a warm-blooded organism in need of such treatment a therapeutically effective amount of an agent of the invention.

Moreover the invention relates to a pharmaceutical composition comprising an agent of the invention in association with at least one pharmaceutical carrier or diluent.

The pharmaceutical compositions according to the invention are compositions for enteral, such as nasal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmacokinetic data, the disease to be treated and the mode of administration.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The agents of the invention may alternatively be administered e.g. topically in the form of a cream, gel or the like, or by inhalation, e.g. in dry powder form.

Examples for compositions comprising an agent of the invention include, e.g. a solid dispersion, an aqueous solution, e.g. containing a solubilising agent, a microemulsion and a suspension of an agent of the invention. The composition may be buffered to a pH in the range of e.g. from 3.5 to 9.5, by a suitable buffer.

The pharmaceutical compositions of the present invention are prepared in a manner known per se, for example by means of conventional dissolving, lyophilizing, mixing, granulating or confectioning processes.

The agents of the invention can be administered either alone, or in combination with other pharmaceutical agents effective in the treatment of conditions mentioned above.

For the indication pain, the agents of this invention can be used in combination with analgesic agents (opiates) or with non-steroidal anti-inflammatory drugs (NSAIDs) such as Rofecoxib (Vioxx®), Celecoxib (Celebrex®) or Lumiracoxib (Prexige®).

For the indication nicotine use disorders, the agents of the invention can be used in combination with bupropione (Zyban®).

The preferred agents of the invention include the (−)-(3aR,4S,7aR)-4-hydroxy-4-m-tolylethynyl-octahydro-indole-1-carboxylic acid methyl ester in free base or pharmaceutically acceptable acid addition salt form.

Said compound inhibits the quisqualate-induced inositol phosphate turnover in hmGlu5 expressing cells with an $IC_{50}$ concentration of 30 nM. With the same compound, a stress-induced hyperthermia of 0.92±0.09° C. was reduced to 0.56±0.06° C. at 0.1 mg/kg p.o., to 0.42±0.06° C. at 1 mg/kg p.o. and to 0.18±0.05° C. at 10 mg/kg p.o. (p<0.001 in each case).

The following non-limiting Examples illustrate the invention.

EXAMPLE 1

(−)-(3aR,4S,7aR)-4-Hydroxy-4-m-tolylethynyl-octahydro-indole-1-carboxylic acid methyl ester a) 1,5,6,7-Tetrahydro-indol-4-one (38.4 g, 28.1 mmol), di-tert-butyldicarbonate (66 g; 302 mmol) and potassium tert-butylate (6 g; 62.5 mmol) in 1 l tetrahydrofuran are heated under reflux for 2 h. After cooling at room temperature the reaction mixture is poured on brine (1 l) and extracted with tert.-butylmethylether (4×500 ml). The combined organic phases are dried over $Na_2SO_4$, filtered and evaporated in vacuo. 51 g of yellowish oil are isolated and purified by column chromatography on silica gel (600 g; eluent hexane/ethylacetate 8:2 v/v). 30.5 g (92%) of 1,5,6,7-Tetrahydro-indol-4-one-1-carboxylic acid tert.butyl ester as white crystals are isolated (mp 84-86° C.).

b) 1,5,6,7-Tetrahydro-indol-4-one-1-carboxylic acid tert-butyl ester (60 g; 255 mmol) and 15 g of 5% Pt on charcoal (given in three portions of 5 g each; 24 h, 48, 72 h) in 1 l of methanol are hydrogenated (1 bar) at room temperature under stirring for 92 h. The mixture is filtered and the solvent evaporated in vacuo. The residual brownish oil is purified by chromatography on silica gel to yield (3aRS,4SR,7aRS)-4-hydroxy-octahydro-indole-1-carboxylic acid tert-butyl ester as a yellowish oil (41.3 g; yield=67%).

c) To a solution of oxalylchloride (1.54 ml; 17.6 mmol) in THF (320 ml) cooled to −60° C. a solution of DMSO (2.28 ml; 32 mmol) in THF (32 ml) is added dropwise under stirring. After 5 min a solution of (3aRS,4SR,7aRS)-4-hydroxy-octahydro-indole-1-carboxylic acid tert-butyl ester (3.96 g; 16.4 mmol) in THF (64 ml) is added and the reaction mixture stirred for 100 min at −60° C. Triethylamine (11.2 ml; 80 mmol) is added and the cooling bath removed and the reaction mixture stirred for further 60 min. The reaction mixture is diluted with ethylacetate (1 l) and washed with sat. $NaHCO_3$ (150 ml). The water phase is extracted with ethylacetate (300 ml). The combined organic phases are dried over $Na_2SO_4$, filtered and evaporated in vacuo. The residue is purified by column chromatography on silica gel (150 g) and the fractions containing the desired compound are collected and evaporated in vacuo to yield (3aRS,7aRS)-4-Oxo-octahydro-indole-1-carboxylic acid tert-butyl ester (2.51 g; yield=65%).

d1) 4 g of (3aRS,7aRS)-4-oxo-octahydro-indole-1-carboxylic acid tert-butyl ester are dissolved in 200 ml of hexane-ethanol 80:20 (v/v). This solution is injected via the pump on a 5 cm by 50 cm Chiralpak AD column (Daicel Chemical Industries). The chromatography is achieved at room temperature at a flow-rate of 100 ml/min and UV detection is performed at 210 nm. The mobile phase consists of a mixture of hexane-ethanol 80:20 (v/v). Under the applied chromatographic conditions, the (+)-enantiomer is isolated from a first fraction collected between 11 and 18 min, and the (−)-enantiomer from a second fraction collected between 20 and 40 min. After 6 injections of a total of 27 g of racemate, the fractions containing the corresponding enantiomers are combined to yield 12.55 g of (+)-enantiomer and 12.23 g of (−)-enantiomer, with an enantiomeric purity of 99% and 99.9%, respectively. The enantiomeric purity is determined on an analytical Chiralpak AD column (0.4×25 cm); mobile phase, hexane-ethanol 90:10 (v/v). (−)-(3aR,7aR)-4-oxo-octahydro-indole-1-carboxylic acid tert-butyl ester ($[\alpha]_D$=−111.6); -(+)-(3aS,7aS)-4-oxo-octahydro-indole-1-carboxylic acid tert-butyl ester ($[\alpha]_D$=+105.2).

d2a) Alternatively (−)-(3aR,7aR)-4-oxo-octahydro-indole-1-carboxylic acid tert-butyl ester can be obtained via the following procedure:

To 11.76 g (47.16 mmol) (3aRS,4SR,7aRS)-4-hydroxy-octahydro-indole-1-carboxylic acid tert-butyl ester in 50 ml TBME and 30 g (34.8 mmol) vinyl acetate, 0.5 g of immobilized lipase from *Candida antarctica* (Novozyme 435) is added and the mixture is stirred at room temperature for 24 h. After filtration of the mixture, the solvent is removed and the obtained oily residue is purified by flash chromatography. The acetate (3aS,4R,7aS)-4-acetoxy-octahydro-indole-1-carboxylic acid tert-butyl ester is isolated in 47% yield with an optical purity of >99% (GC, $[\alpha]_D^{20}$=+54.6° c=1, MeOH). The recovered alcohol (3aR,4S,7aR)-4-hydroxy-octahydro-indole-1-carboxylic acid tert-butyl ester is obtained in 51% yield and >95% e.e.(GC, $[\alpha]_D^{20}$=−41.3° c=1, MeOH). Further purification by MPLC affords the alcohol with 99.5% purity and 99.5% e.e.

d2b) The alcohol (3aR,4S,7aR)-4-hydroxy-octahydro-indole-1-carboxylic acid tert-butyl ester is oxidized to the ketone as described in Example 1c) to yield (−)-(3aR,7aR)-4-oxo-octahydro-indole-1-carboxylic acid tert-butyl ester.

e) To a solution of 1-ethynyl-3-methyl-benzene (3.248 g; 28 mmol) in THF (168 ml) cooled to −20° C., a solution of butyllithium (17.5 ml; 28 mmol; 1.6M in hexane) is added. The reaction mixture is stirred at −20° C. for 2 h then a solution of (−)-4-oxo-octahydro-indole-1-carboxylic acid tert-butyl ester (3.346 g; 14 mmol) in THF (70 ml) is added and the reaction mixture further stirred at 0-5° C. After 2 h the reaction mixture is diluted with ethylacetate (900 ml) and washed with sat. $NaHCO_3$ (2×90 ml). The aqueous phase is extracted with ethylacetate (400 ml). The combined organic phases are dried over $Na_2SO_4$, filtered and evaporated in vacuo. The residue is purified by column chromatography on silica gel (300 g) and the fractions containing the desired compound are collected and evaporated in vacuo to yield (−)-(3aR,4S,7aR)-4-Hydroxy-4-m-tolylethynyl-octahydro-indole-1-carboxylic acid tert-butyl ester (4.27 g; yield=85%). 1H-NMR (400 MHz; DMSO-D6): δ 7.3-7.1 (m, 4H), 5.5 (d, J=5 Hz, 1H), 3.85-3.65 (m, 1H), 3.35-3.25 (m, 1H), 3.25-3.1 (m, 1H), 2.6-2-45 (m, 1H), 2.28 (s, 3H), 1.9-1.4 (m, 7H), 1.36 (s, 9H), 1.13-0.98 (m, 1H).

f) (−)-(3aR,4S,7aR)-4-Hydroxy-4-m-tolylethynyl-octahydro-indole-1-carboxylic acid tert-butyl ester (4.27 g; 12 mmol) is dissolved in a solution of 1M HCl in ethylacetate (240 ml) and stirred at room temperature for 6 h. After completion of of the hydrolysis (TLC) the solvent is evaporated in vacuo to yield (−)-(3aR,4S,7aR)-4-Hydroxy-4-m-tolylethynyl-octahydro-indole hydrochloride (3.39 g; yield=93%). m.p.=181-183° C.

g) (−)-(3aR,4S,7aR)-4-Hydroxy-4-m-tolylethynyl-octahydro-indole hydrochloride (3.38 g; 11.6 mmol) is suspended in $CH_2Cl_2$ (174 ml), triethylamine (3.6 ml; 25.52 mmol) is added and the mixture is cooled to 5° C.

Methylchloroformate (1.2 ml; 15.08 mmol) is added dropwise. After completion of the addition, the cooling bath is removed and the solution stirred for 2 h. The reaction mixture is diluted with $CH_2Cl_2$ (250 ml) and washed with brine (1×50 ml). The aqueous phase is extracted with $CH_2Cl_2$ (50 ml), the combined organic phases are dried over $Na_2SO_4$, filtered and the solvent evaporated in vacuo. The residue is column chromatographed on silica gel (240 g), eluent toluene/acetone 9:1 v/v. The fractions containing the desired compound are collected and evaporated in vacuo to yield 3.39 g of (−)-(3aR,4S,7aR)-4-hydroxy-4-m-tolylethynyl-octahydro-indole-1-carboxylic acid methyl ester (yield=90%). M.p.=110-112° C. $[\alpha]_D$=−20.6 (c=1, methanol).

Following the same procedure, the following compounds are obtained:

EXAMPLE 1a (−)-(3aR,4S,7aR)-4-Hydroxy-4-m-tolylethynyl-octahydro-indole-1-carboxylic acid ethyl ester M.p.=118-121° C.

EXAMPLE 1b (−)-(3aR,4S,7aR)-Furan-2-yl-(4-hydroxy-4-m-tolylethynyl-octahydro-indol-1-yl)-methanone M.p.=195.5-196.5° C.

EXAMPLE 1c (±)-(3aRS,4SR,7aRS)-4-(3-Chlorophenylethynyl)-4-hydroxy-octahydro-indole-1-carboxylic acid ethyl ester 1H NMR (400 MHz; CDCl3): 1.27(t, 3H), 1.60-1.80(m, 4H), 1.88-2.11(m, 5H), 2.27(m, 1H), 3.38(m, 1H), 3.54(m, 1H), 4.10(m, 2H), 7.22-7.31(m, 3H), 7.40(m,1H).

EXAMPLE 1d (±)-(3aRS,4SR,7aRS)-4-(3-Fluoro-phenylethynyl)-4-hydroxy-octahydro-indole-1-carboxylic acid ethyl ester HPLC-MS: 354 (M+Na).

EXAMPLE 1e (3aRS,4SR,7aRS)-4-Hydroxy-4-phenylethynyl-octahydro-indole-1-carboxylic acid(S)(tetrahydrofuran-3-yl)ester

ES-MS (+): 356 (M+1).

EXAMPLE 1f (3aRS,4SR,7aRS)-4-Hydroxy-4-phenylethynyl-octahydro-indole-1-carboxylic acid(R)(tetrahydrofuran-3-yl)ester

ES-MS (+): 356 (M+1).

EXAMPLE 1g (3aRS,4SR,7aRS)-4-Hydroxy-4-(3-chlorophenyl-ethynyl)-octahydro-indol-1-carboxylic acid-(S)(tetrahydrofuran-3yl)ester 1H NMR (400 MHz; CHCl3): 7.39 (s, 1H), 7.25 (m, 3H), 5.27 (m, 1H),4.10-3.85 (m, 5H), 3.55 (m, 1H), 3.4 (m, 1H), 2.7 (m, 1H), 2.3 (s, 1H), 2.2-1.9 (m, 6H), 1.8-1.6 (m, 3H), 1.07 (m, 1H).

EXAMPLE 1h (±)-(3aRS,4SR,7aRS)-4-Hydroxy-4-m-tolylethynyl-octahydro-indole-1-carboxylic acid ethyl ester ES-MS (+): 328.2 [M+1], m.p.=123-124° C.

EXAMPLE 1i (±)-(3aRS,4SR,7aRS)-4-(4-Fluoro-phenylethynyl)-4-hydroxy-octahydro-indole-1-carboxylic acid ethyl ester ES-MS (+): 332.2, m.p.=115-116° C.

EXAMPLE 1j (±)-(3aRS,4SR,7aRS)-4-(3-chlorophenylethynyl)-4-hydroxy-1-methanesulfonyl-octahydro-indole NMR (CDCl3): 7.41 (s,1H), 7.30 (m,3H), 3.93 (m,1H), 3.57 (m,1H), 3.35 (m,1H), 2.85 (s,3H), 2.69 (m,1H), 2.35 (bs,1H), 2.14 (m,1H), 2.0 (m,1H), 1.90, m,1H), 1.82-1.65 (m,4H), 1.35 (m,1H). HPLC: 1 peak, 99%

EXAMPLE 2

(±)-(3aRS,7aRS)-4-Phenylethynyl-2,3,3a,6,7,7a-hexahydro-indole-1-carboxylic acid ethyl ester and (±)-(RS)-4-Phenylethynyl-2,3,5,6,7,7a-hexahydro-indole-1-carboxylic acid ethyl ester A solution of 4-hydroxy-4-phenylethynyl-octahydro-indole-1-carboxylic acid ethyl ester (1.0 g, 3.19 mmol), triethylamine (2.2 ml, 16 mmol) and phosphorous oxychloride 0.877 ml, 10 mmol) is heated to 40° C. for 4 hours. The dark mixture is cooled to 0° C. and treated with 1M sodium hydroxide (5 ml) and then acidified with a 10% aqueous citric acid solution. The mixture is extracted with dichloromethane, the organic extracts are washed with brine, dried over anhydrous magnesium sulfate and evaporated in vacuo. The residue is chromatographed on silica with hexane and diethyl ether (4:1 v/v). The first product containing fractions afforded (±)-(RS)-4-phenylethynyl-2,3,5,6,7,7a-hexahydro-indole-1-carboxylic acid ethyl ester (10 mg, 1%) as a yellowish oil. 1H-NMR (400 MHz; CDCl3): 7.44 (m, 2H), 7.32 (m, 3H), 4.24-3.97 (m, 3H), 3.8 (m, 1H), 3.25 (m, 1 H), 2.93 (m, 1H), 2.56 (m, 1H), 2.28 (m, 2H), 1.90 (m, 1H), 1.60 (m, 2H), 1.28 (t, J=7 Hz, 3H), 1.14 (m,1H). ES-MS (+): 296.1. After collecting a mixture of the two products (475 mg, 50%), the third product containing fractions yielded (±)-(3RS,7aRS)-4-phenylethynyl-2,3,3a,6,7,7a-hexahydro-indole-1-carboxylic acid ethyl ester (64 mg, 7%) as a yellowish oil. 1H-NMR (400 MHz; CDCl3): 7.43 (m, 2H), 7.31 (m, 3H), 6.27 (m, 1H), 4.15 (m, 2H), 4.01-3.83 (m, 1H), 3.46(m, 2H), 2.82 (m, 1H), 2.37-1.82 (m, 5H), 1.57 (m, 1H), 1.27 (t, J=7 Hz, 3H). ES-MS (±): 296.2.

Following the same synthetic procedure the following examples can be made:

EXAMPLE 2a (±)-(3RS,7aRS)-2,2,2-Trifluoro-1-(4-phenylethynyl-2,3,3a,6,7,7a-hexahydro-indol-1-yl)-ethanone ES-MS (+): 320.3 (M+1), $R_f$=0.62 (TLC silica gel, hexane/ethyl acetate 2:1).

EXAMPLE 2b (±)-(RS)-4-m-Tolylethynyl-2,3,5,6,7,7a-hexahydro-indole-1-carboxylic acid ethyl ester ES-MS (+): 310.2 (M+1), $R_f$=0.55 (TLC silica gel, hexane/ethyl acetate 2:1).

EXAMPLE 2c (±)-(3RS,7aRS)-4-m-Tolylethynyl-2,3,3a,6,7,7a-hexahydro-indole-1-carboxylic acid ethyl ester ES-MS (+): 310.2 (M+1), $R_f$=0.59 (TLC silica gel, hexane/ethyl acetate 2:1).

EXAMPLE 2d (±)-(3RS,7aRS)-4-(4-Chloro-phenylethynyl)-2,3,3a,6,7,7a-hexahydro-indole-1-carboxylic acid ethyl ester ES-MS (+): 330.2 (M+1), $R_f$=0.56 (TLC silica gel, hexane/ethyl acetate 2:1).

EXAMPLE 2e (±)-(3RS,7aRS)-4-(2-Fluoro-phenylethynyl)-2,3,3a,6,7,7a-hexahydro-indole-1-carboxylic acid ethyl ester ES-MS (+): 314.2 (M+1), $R_f$=0.42 (TLC silica gel, hexane/ethyl acetate 2:1).

EXAMPLE 2f (±)-(3RS,7aRS)-4-(3-Fluoro-phenylethynyl)-2,3,3a,6,7,7a-hexahydro-indole-1-carboxylic acid ethyl ester

ES-MS (+): 314.2 (M+1).

EXAMPLE 2g (±)-(RS)-4-(3-Fluoro-phenylethynyl)-2,3,5,6,7,7a-hexahydro-indole-1-carboxylic acid ethyl ester ES-MS (+): 336.2 (M+Na).

EXAMPLE 2h (±)-(3RS,7aRS)-4-(3-Methoxy-phenylethynyl)-2,3,3a,6,7,7a-hexahydro-indole-1-carboxylic acid ethyl ester ES-MS (+): 348.2 (M+Na).

EXAMPLE 2i (±)-(RS)-4-(3-Methoxy-phenylethynyl)-2,3,5,6,7,7a-hexahydro-indole-1-carboxylic acid ethyl ester ES-MS (+): 348.2 (M+Na).

EXAMPLE 3

(±)-(3aRS,4RS,7aSR)-4-Hydroxy-4-phenylethynyl-octahydro-isoindole-2-carboxylic acid ethyl ester a) A solution of 716 g acetic acid (±)-(3aRS,4RS,7aRS)-2-benzyl-1,3-dioxo-2,3,3a,4,7,7a-hexahydro-1H-isoindol-4-yl ester [CAN 153255-27-7, see J.Chem.Soc. Perkin Trans I (1993), 1925-1929] in 3.5 l tetrahydrofuran is added dropwise to 300 g lithium aluminum hydride in 3.5 l tetrahydrofuran at 50° C. Thereafter the mixture is refluxed for 1 h, then cooled to 0° C. 300 ml water, followed by 300 ml 15% aqueous sodium hydroxide solution and again 600 ml water is added at max 15° C. After filtration about 550 g slightly brown crystallizing oil, consisting of (±)-(3aRS,4SR,7aSR)-2-benzyl-2,3,3a,4,7,7a-hexahydro-1H-isoindol-4-ol is obtained. M.p. 69-71C.

b) 1020 g (±)-(3aRS,4SR,7aSR)-2-benzyl-2,3,3a,4,7,7a-hexahydro-1H-isoindol-4-ol and 560 g oxalic acid dihydrate are dissolved in 18 l water, then hydrogenated using 200 g 10% palladium on charcoal catalyst at 100° C., 100 atm for 16 h. After filtration of the catalyst the solution is concentrated to a volume of 6 l and 4.5 l dichloromethane are added. 810 g potassium hydroxide pellets are added portionwise, then ethyl chloro formate is added dropwise at a temperature not exceeding 30° C. The reaction mixture is extracted with dichloromethane, evaporated to yield 827 g (±)-(3aRS,4SR,7aSR)-4-hydroxy-octahydro-isoindole-2-carboxylic acid ethyl ester as slightly brown oil; purity by GC: 98.5%.

c) To 6.6 g oxalic chloride in 300 tetrahydrofuran at –60° C. 7.4 g dimethylsulfoxide are added, then stirred for 15 min. 10 g (±)-(3aRS,4SR,7aSR)-4-hydroxy-octahydro-isoindole-2-carboxylic acid ethyl ester in 50 ml tetrahydrofuran is added at –60° C., followed by 23 g triethylamine and allowed to warm at rt. The suspension is filtered, 400 ml ethyl acetate is added to the filtrate and the mixture washed with 3 times 400 ml water. Organic phases are dried with sodium sulfate and evaporated yielding 9.9 g (±)-(3aRS,7aSR)-4-oxo-octahydro-isoindole-2-carboxylic acid ethyl ester as crude brown oil. ES-MS(–): 210 (M–1), RP-HPLC: single peak.

d) 2.1 g (±)-(3aRS,7aSR)-4-oxo-octahydro-isoindole-2-carboxylic acid ethyl ester in 10 ml tetrahydrofuran is added at –10° C. to 20 ml of 1M lithium phenylacetylide in tetrahydrofuran within 10 min. After 16 h at room temperature 100 ml saturated aqueous ammonium chloride solution is added, the mixture extracted with ethyl acetate, solvents dried over sodium sulfate and evaporated. The product is flash-chromatographed on silicagel with hexane/ethyl acetate (2:1). 2.2 g (±)-(3aRS,4RS,7aSR)-4- hydroxy-4-phenylethynyl-octahydro-isoindole-2-carboxylic acid ethyl ester are obtained as brown oil. ES-MS (+): 314 (M+1), RP-HPLC: single peak.

Following the same procedure the following compounds are obtained:

EXAMPLE 3a (±)-(3aRS,4RS,7aSR)-4-Hydroxy-4-m-tolylethynyl-octahydro-isoindole-2-carboxylic acid ethyl ester ES-MS(+): 328 (M+1), RP-HPLC: single peak.

EXAMPLE 3b (±)-(3aRS,4RS,7aSR)-4-Hydroxy-4-p-tolylethynyl-octahydro-isoindole-2-carboxylic acid ethyl ester HPLC-MS: single peak, 350 (M+Na).

EXAMPLE 3c (±)-(3aRS,4RS,7aSR)-4-(3-Cyano-phenylethynyl)-4-hydroxy-octahydro-isoindole-2-carboxylic acid ethyl ester HPLC-MS: single peak, 361 (M+Na).

EXAMPLE 3d (±)-(3aRS,4RS,7aSR)-4-Hydroxy-4-(3-methoxy-phenylethynyl)-octahydro-isoindole-2-carboxylic acid ethyl ester ES-MS(+): 344 (M+1), HPLC: single peak.

EXAMPLE 3e (±)-(3aRS,4RS,7aSR)-4-(3-Fluoro-phenylethynyl)-4-hydroxy-octahydro-isoindole-2-carboxylic acid ethyl ester ES-MS(+): 332 (M+1), HPLC: single peak.

EXAMPLE 4

(±)-(3aRS,4RS,7aSR)-4-Hydroxy-4-phenylethynyl-octahydro-isoindole-2-carboxylic acid tert-butyl ester a) Crude (±)-(3aRS,7aSR)-4-oxo-octahydro-isoindole-2-carboxylic acid tert-butyl ester is prepared in a 4-step procedure without purification: Starting from (3aSR,7aRS)-4-oxo-octahydro-isoindole-2-carboxylic acid ethyl ester: 1) Ketal formation with ethylene glycole in toluene/p-TsOH. 2) Removal of the ethyl carbamate using KOH in MeOH in sealed tube at 100° C. 3) Removal of ketal using 4N aqueous hydrochloric acid in acetone at room temperature. 4) Formation of the tert.-butyl carbamate using BOC-anhydride, K$_2$CO$_3$, in dichloromethane.

b) Reaction to (±)-(3aRS,4RS,7aSR)-4-hydroxy-4-phenylethynyl-octahydro-isoindole-2-carboxylic acid tert-butyl ester as described in Example 3d). ES-MS(+): 342 (M+1), RP-HPLC: single peak.

Following the same procedure, the following compound is obtained:

EXAMPLE 4a (±)-(3aRS,4RS,7aSR)-4-Hydroxy-4-m-tolylethynyl-octahydro-isoindole-2-carboxylic acid tert-butyl ester ES-MS(+): 356 (M+1), RP-HPLC: single peak.

EXAMPLE 5

(±)-(3aRS,4RS,7aSR)-4-Hydroxy-4-m-tolylethynyl-octahydro-isoindole-2-carboxylic acid methyl ester a) 1 g of (±)-(3aRS,4RS,7aSR)-4-Hydroxy-4-m-tolylethynyl-octahydro-isoindole-2-carboxylic acid tert-butyl ester is treated with ca. 1N HCl in ethyl acetate at room temperature for 18 h, then washed with saturated sodium hydrogencarbonate solution. The organic phase is dried over Na2SO4 and evaporated. Purification by prep-HPLC. (±)-(3aRS,4RS,7aSR)-4-m-tolylethynyl-octahydro-isoindol-4-ol is obtained.

b) 60 mg of (±)-(3aRS,4RS,7aSR)-4-m-tolylethynyl-octahydro-isoindol-4-ol, 25 mg methyl chloroformate and 250 mg polymer-supported Hünig's base in 5 ml dichloromethane are stirred at room temperature for 18 h, then filtered and evaporated, followed by prep-HPLC purification to yield (±)-(3aRS,4RS,7aSR)-4-Hydroxy-4-m-tolylethynyl-octahydro-isoindole-2-carboxylic acid methyl ester. HPLC-MS: 336 (M+Na).

Following the same procedure, the following compounds are obtained:

EXAMPLE 5a (±)-(3aRS,4RS,7aSR)-Furan-2-yl-(4-hydroxy-4-m-tolylethynyl-octahydro-isoindol-2-yl)-methanone HPLC-MS: 372 (M+Na).

EXAMPLE 5b (±)-(3aRS,4RS,7aSR)-Cyclopropyl-(4-hydroxy-4-m-tolylethynyl-octahydro-isoindol-2-yl)-methanone HPLC-MS: 346 (M+Na).

EXAMPLE 5c (±)-(3aRS,4RS,7aSR)-(4-Hydroxy-4-m-tolylethynyl-octahydro-isoindol-2-yl)-pyridin-3-yl-methanone HPLC-MS: 361 (M+1), 383 (M+Na).

EXAMPLE 6

(±)-((1SR,3SR)-3-Hydroxy-3-m-tolylethynyl-cyclohexyl)methyl-carbamic acid methyl ester and (±)-((1RS,3SR)-3-hydroxy-3-m-tolylethynyl-cyclohexyl)-methyl-carbamic acid methyl ester a) To a solution of 3-methylamino-cyclohex-2-enone (1.35 g, 10.8 mmol; CAS 55998-74-8) and triethylamine (4.5 ml, 32.4 mmol) in dichloromethane (20 ml) is added methyl chloroformate (2.5 ml, 32.4 mmol) at 0° C. during 15 minutes. After 45 minutes the reaction mixture is diluted with dichloromethane and washed three times with citric acid (10% w/v). The organic phase is concentrated in vacuo and the residue is treated with K$_2$CO$_3$ (3.0 g, 21.6 mmol) in water/methanol (1:1 v/v, 20 ml) for 15 minutes. The reaction mixture is concentrated in vacuo and the residue partitioned between water and dichloromethane and after concentration in vacuo the mixture is chromatographed on silica gel (100 g) with hexane/ethyl acetate (1:1 v/v) as eluent. The product methyl-(3-oxo-cyclohex-1-enyl)-carbamic acid methyl ester is obtained as a pale orange oil. NMR (400 MHz; CDCl$_3$): 5.68 (s, 1H), 3.79 (s, 3H), 3.20 (s,3H), 2.82 (t, J=6.5 Hz, 2H), 2.39 (t, J=6.5 Hz, 2H), 2.00 (quint., J=6.5 Hz, 2H).

b) A solution of methyl-(3-oxo-cyclohex-1-enyl)-carbamic acid methyl ester (412 mg, 2.2 mmol) in methanol (20 ml) is hydrogenated with Pd/C (10%, 80 mg, 1 bar). After filtration the crude product is chromatographed on silica gel (30 g) with hexane/ethyl acetate (1:1 v/v) as eluent. Methyl-(3-oxo-cyclohexyl)-carbamic acid methyl ester is obtained as a colorless oil. NMR (400 MHz; CDCl$_3$): 4.23 (br, 1H), 3.69 (s, 3H), 2.83 (br,s, 3H), 2.57-2.34 (m, 3H), 2.21 (td, J=14 Hz, J=6 Hz, 1H), 2.05 (m, 1H), 1.91 (m, 1H), 1.80 (qd, J=12.5 Hz, J=3.5 Hz, 1H), 1.6 (m, 1H).

c) The reaction of methyl-(3-oxo-cyclohexyl)-carbamic acid methyl ester with lithium m-tolylacetylide is performed as in example 1. After chromatography on silicagel with hexane/ethyl acetate (gradient 4:1 to 1:1 v/v) as eluent the title compound (±)-((1SR,3SR)-3-hydroxy-3-m-tolyl-ethynyl-cyclohexyl)-methyl-carbamic acid methyl ester (yield 24%) is first eluted (R$_f$=0.62 (TLC silica gel, hexane/ethyl acetate 1:1), HPLC-MS: 324.2 (M+Na)$^+$) followed by (±)-((1RS,3SR)-3-hydroxy-3-m-tolyethy-nyl-cyclohexyl)-methyl-carbamic acid methyl ester (yield 50%, R$_f$=0.49 (TLC silica gel, hexane/ethyl acetate 1:1), HPLC-MS: 324.2 (M+Na)$^+$).

Following the same procedure the following compounds are obtained:

EXAMPLE 6a (±)-(1RS,3SR)-((3-Hydroxy-3-m-tolylethynyl-cyclo-hexyl)-(4-methoxy-benzyl)-carbamic acid ethyl ester HPLC-MS: 444.2 (M+Na)$^+$.

EXAMPLE 6b (±)-(1RS,3RS)-((3-Hydroxy-3-m-tolylethynyl-cyclo-hexyl)-(4-methoxy-benzyl)-carbamic acid ethyl ester HPLC-MS: 444.2 (M+Na)$^+$.

EXAMPLE 6c (±)-[(1RS,3SR)-3-Hydroxy-3-(3-methoxy-phenyl-ethynyl)-5,5-dimethyl-cyclohexyl]-methyl-carbamic acid methyl ester HPLC-MS: 368.2 (M+Na)$^+$.

EXAMPLE 6d (±)-(1RS,3SR)-(3-Hydroxy-5,5-dimethyl-3-m-tolyl-ethynyl-cyclohexyl)-methyl-carbamic acid methyl ester HPLC-MS: 352.2 (M+Na)$^+$.

EXAMPLE 6e (±)-[(1RS,3SR)-3-(3-Fluoro-phenylethynyl)-3-hy-droxy-5,5-dimethyl-cyclohexyl]-methyl-carbamic acid methyl ester HPLC-MS: 356.2 (M+Na)$^+$.

EXAMPLE 6f (±)-[(1RS,3RS)-3-(3-Fluoro-phenylethynyl)-3-hy-droxy-cyclohexyl]-methyl-carbamic acid methyl ester HPLC-MS: 328.2 (M+Na)$^+$.

EXAMPLE 6g (±)-[(1RS,3SR)-3-(3-Fluoro-phenylethynyl)-3-hy-droxy-cyclohexyl]-methyl-carbamic acid methyl ester HPLC-MS: 328.2 (M+Na)$^+$.

EXAMPLE 6h (±)[(1RS,3RS)-3-Hydroxy-3-(3-methoxy-phenyl-ethynyl)-cyclohexyl]-methyl-carbamic acid methyl ester HPLC-MS: 340.2 (M+Na)$^+$.

EXAMPLE 6i (±)-[(1RS,3SR)-3-Hydroxy-3-(3-methoxy-phenyl-ethynyl)-cyclohexyl]-methyl-carbamic acid methyl ester HPLC-MS: 340.2 (M+Na)$^+$.

EXAMPLE 6j (±)-[(1RS,3RS)-3-(3-Chloro-phenylethynyl)-3-hy-droxy-cyclohexyl]-methyl-carbamic acid methyl ester R$_f$=0.31 (TLC silica gel, hexane/ethyl acetate 1:1).

EXAMPLE 6k (±)-[(1RS,3SR)-3-(3-Chloro-phenylethynyl)-3-hy-droxy-cyclohexyl]-methyl-carbamic acid methyl ester R$_f$=0.22 (TLC silica gel, hexane/ethyl acetate 1:1).

EXAMPLE 6l (±)-(1RS,3RS)—N-(3-hydroxy-3-m-tolylethynyl-cyclohexyl)-acetamide HPLC-MS: 294.2 (M+Na).

EXAMPLE 6m (±)-(1RS,3SR)—N-(3-hydroxy-3-m-tolylethynyl-cyclohexyl)-acetamide M.p. 152-155° C.

EXAMPLE 6n (±)-(1RS,3RS)-(3-Hydroxy-3-m-tolylethynyl-cyclohexyl)-carbamic acid ethyl ester HPLC-MS: 324.2 (M+Na).

EXAMPLE 6o (±)-(1RS,3SR)-(3-Hydroxy-3-m-tolylethynyl-cyclohexyl)-carbamic acid ethyl ester M.p. 106-107° C.

EXAMPLE 6p (±)-(1RS,3RS)-[3-(3-Fluoro-phenylethynyl)-3-hydroxy-cyclohexyl]-carbamic acid ethyl ester HPLC-MS: 328.2 (M+Na).

EXAMPLE 6q (±)-(1RS,3SR)-[3-(3-Fluoro-phenylethynyl)-3-hydroxy-cyclohexyl]-carbamic acid ethyl ester M.p. 121-123° C.

EXAMPLE 6r (±)-(1RS,3RS)-[3-(3Methoxy-phenylethynyl)-3-hydroxy-cyclohexyl]-carbamic acid ethyl ester HPLC-MS: 340.2 (M+Na).

EXAMPLE 6s (±)-(1RS,3RS)—N-[3-(3-Fluoro-phenylethynyl)-3-hydroxy-cyclohexyl]-acetamide HPLC-MS: 340.2 (M+Na).

EXAMPLE 6t (±)-(1RS,3SR)—N-[3-(3-Fluoro-phenylethynyl)-3-hydroxy-cyclohexyl]-acetamide HPLC-MS: 276.2 (M+1), 298.2 (M+Na).

EXAMPLE 6u (±)-(1RS,3SR)-[3-Hydroxy-3-(3-methoxy-phenylethynyl)-cyclohexyl]-carbamic acid ethyl ester HPLC-MS: 340.2 (M+Na).

EXAMPLE 6v (±)-(1RS,3RS)—N-[3-Hydroxy-3-(3-methoxy-phenylethynyl)-cyclohexyl]-acetamide HPLC-MS: 288.2 (M+1), 310.2 (M+Na).

EXAMPLE 6w (±)-(1RS,3SR)—N-[3-Hydroxy-3-(3-methoxy-phenylethynyl)-cyclohexyl]-acetamide HPLC-MS: 288.2 (M+1), 310.2 (M+Na).

EXAMPLE 6x (±)-(1RS,3RS)-[3-Hydroxy-3-(3-methoxy-phenylethynyl)-cyclohexyl]-carbamic acid tert-butyl ester HPLC-MS: 368.2 (M+Na).

Example 6y (±)-(1RS,3SR)-[3-Hydroxy-3-(3-methoxy-phenylethynyl)-cyclohexyl]-carbamic acid tert-butyl ester HPLC-MS: 368.2 (M+Na).

Example 6z (±)-(1RS,3RS)-(3-Hydroxy-3-m-tolylethynyl-cyclohexyl)-carbamic acid tert-butyl ester HPLC-MS: 352.2 (M+Na).

EXAMPLE 6aa (±)-(1RS,3SR)-(3-Hydroxy-3-m-tolylethynyl-cyclohexyl)-carbamic acid tert-butyl ester HPLC-MS: 352.1 (M+Na).

EXAMPLE 6ab (±)-(1RS,3RS)-(3-(3-Fluoro-phenylethynyl)-3-hydroxy-cyclohexyl)-carbamic acid tert-butyl ester HPLC-MS: 356.2 (M+Na).

EXAMPLE 6ac (±)-(1RS,3SR)-(3-(3-Fluoro-phenylethynyl)-3-hydroxy-cyclohexyl)-carbamic acid tert-butyl ester HPLC-MS: 356.2 (M+Na).

EXAMPLE 6ad (±)-(1RS,3RS)-[3-(3-Fluoro-phenylethynyl)-3-hydroxy-cyclohexyl]-carbamic acid methyl ester HPLC-MS: 314.2 (M+Na).

EXAMPLE 6ae (±)-(1RS,3SR)-[3-(3-Fluoro-phenylethynyl)-3-hydroxy-cyclohexyl]-carbamic acid methyl ester HPLC-MS: 314.2 (M+Na).

EXAMPLE 7

(±)-(3-Phenylethynyl-cyclohex-2-enyl)-carbamic acid ethyl ester and (±)-3-phenylethynyl-cyclohex-3-enyl)-carbamic acid ethyl ester 100 mg (0.35 mmol) (3-hydroxy-3-phenylethynyl-cyclohexyl)-carbamic acid ethyl ester (diasteromeric mixture 2) in 15 mL toluene are treated with 10 mg p-toluene sulfonic acid and stirred 6 hours at 120°. After cooling and addition of 50 ml ethyl acetate, the product is washed with water containing a small amount of sodium bicarbonate, and saline. The organic phase is dried with sodium sulfate, concentrated and column chromatographed using a 3:1 mixture of petroleum ether and ethyl acetate. The first product to come out of the column is (3-phenylethynyl-cyclohex-2-enyl)-carbamic acid ethyl ester (yield, 23%), followed by (3-phenylethynyl-cyclohex-3-enyl)-carbamic acid ethyl ester (yield: 48%)

Racemate 1: $^1$H-NMR (400 MHz): delta=7.41 (m, 2H); 7.30 (m, 3H); 6.04 (s, 1H); 4.63 (broad s, 1H); 4.35 (broad s, 1H); 4.10 (q, 2H); 2.20 (s, 2H); 1.90 (m, 1H); 1.70, (m, 2H); 1.50 (m, 1H); 1.23 (t, 3H).

Racemate 2: $^1$H-NMR (400 MHz): delta=7.40 (m, 2H); 7.30 (m, 3H); 6.19 (s, 1H); 4.68 (broad s, 1H); 4.10 (q, 2H); 3.92 (broad s, 1H); 2.61 (d, 1H); 2.28 (broad s, 2H); 2.12, 1.85, 1.59 (3m, 3H); 1.23 (t, 3H).

EXAMPLE 8

(±)-Methyl-(3-phenylethynyl-cyclohex-3-enyl)-carbamic acid ethyl ester 22 mg (0.082 mmol) (3-phenylethynyl-cyclohex-3-enyl)-carbamic acid ethyl ester are dissolved in 2 ml DMF and 1 mL THF. 8 mg (0.165 mmol) of a 60% dispersion of NaH in oil is added and the mixture stirred under argon for 90 minutes at room temperature. The reaction mixture is cooled to 0°, and 16 microliters MeI in 0.5 ml THF are added dropwise. After stirring one hour at room tenmperature, the reaction mixture is cooled to 0° again, ice is added and the crude product extracted with ethyl acetate, washed with water and saline, dried with sodium sulfate and column chromatographed using a 4:1 mixture of petroleum ether and ethyl acetate. Yield: 43% .

$^1$H-NMR (400 MHz): delta=7.40 (m, 2H); 7.30 (m, 3H); 6.18 (s, 1H); 4.22 (broad m, 1H); 4.15 (q, 2H); 2.8 (broad s, 3H); 2.35 (broad s, 4H); 1.80-1.60 (m, 1H); 1.15 (t, 3H).

EXAMPLE 9

(±)-(4aRS,5RS,8aSR)-5-Hydroxy-5-phenylethynyl-octahydro-quinoline-1-carboxylic acid ethyl ester a) To the mixture of (±)-(4aRS,8aSR)-octahydro-quinolin-5-one oxalate (1.50 g, 6.17 mmol), toluene (5 ml) and water (5 ml) is added solid potassium carbonate. After stirring for a few minutes ethyl chloroformate (0.71 ml, 7.4 mmol) is added and the reaction mixture is then stirred at room temperature for 3 hours. The organic phase is separated and the aqueous phase extracted with dichloromethane (3×10 ml). The combined organic phases are dried over magnesium sulphate and concentrated in vacuo to yield 1.22 g (88%) of (±)-(4aRS,8aSR)-5-Oxo-octahydro-quinoline-1-carboxylic acid ethyl ester. 1H NMR (400 MHz; CDCl3): 1.28 (t, 3H), 1.40 1.70 (m, 3H), 1.72-1.90 (m,1H), 2.0-2.20 (m, 3H), 2.30-2.48 (m, 3H), 2.55 (td, 1H), 3.32 (td, 1H), 3.50 (m, 2H), 4.12 (q, 2H).

b) To a solution of (±)-(4aRS,8aSR)-5-oxo-octahydro-quinoline-1-carboxylic acid ethyl ester (0.372 g, 1.65 mmol) in THF (15 ml) is added a solution of lithium phenylacetylide in THF (3.30 ml, 3.30 mmol; 1.0M solution in THF) at −50 C. The reaction mixture is then stirred for 1.5 hours at −50 C and then allowed to warm to room temperature. The reaction mixture is diluted with diethyl ether (100 ml), washed with saturated sodium bicarbonate solution (2×10 ml), water (10 ml), dried over magnesium sulfate and then concentrated in vacuo. Purification of the crude product (0.860 g) using silica gel chromatography (ethylacetate/hexane 1:3 v/v ) give (±)-(4aRS,5RS,8aSR)-5-hydroxy-5-phenylethynyl-octahydro-quinoline-1-carboxylic acid ethyl ester.(0.144 g, 26.7%).

Following the same procedure the following compounds are obtained:

EXAMPLE 9a (±)-[(4aRS,5SR,8aSR)-5-(3-Chloro-phenylethynyl)-5-hydroxy-octahydro-quinolin-1-yl]-furan-2-yl-methanone NMR (DMSO-D6, 500 MHz): 7.84 (s,1H), 7.45 (m,4H), 6.95 (d,1H), 6.63 (d,1H), 5.51 (s,1H), 4.03 (m,1H), 3.94 (m,1H), 3.32 (m,1H), 2.06 (m,1H), 2.04 (m,1H), 1.96 (m,1H), 1.94 (m,1H), 1.85 (m,1H), 1.74 (m.2H), 1.71 (m,1H), 1.60 (m,1H), 1.50 (m,1H), 1.41 (m,1H).

EXAMPLE 9b (±)-[(4aRS,5RS,8aSR)-5-(3-Chloro-phenylethynyl)-5-hydroxy-octahydro-quinolin-1-yl]-furan-2-yl-methanone NMR (DMSO-D6, 500 MHz): 7.83 (s,1H), 7.43 (m,4H), 6.95 (d,1H), 6.62 (m,1H), 5.77 (s,1H), 3.99 (m,1H), 3.90 (m,1H), 3.31 (m,1H), 2.12 (m,1H), 2.06 (m,1H), 1.97 (m,1H), 1.88 (m,1H), 1.83 (m,1H), 1.77 (m,1H), 1.66 (m,1H), 1.59 (m,2H), 1.46 (m,1H), 1.22 (m,1H).

EXAMPLE 9c (±)-(4aRS,5RS,8aSR)-5-(3-Chloro-phenylethynyl)-5-hydroxy-octahydro-quinoline-1-carboxylic acid tert-butyl ester NMR (CDCl3): 7.42 (d,J=1.1 Hz, 1H), 7.32 (m,3H), 3.55 (m,1H), 3.48 (m,1H), 3.10 (m,1H), 2.08 (m,3H), 1.90 (m,1H), 1.8-1.6 (m,7H), 1.46 (s,9H), 1.38 (m,1H).

EXAMPLE 9d (±)-[(4aRS,5SR,8aSR)-5-(3-Chloro-phenylethynyl)-5-hydroxy-octahydro-quinolin-1-yl]-morpholin-4-yl-methanone

LC-MS, M+1=403.1

EXAMPLE 9e (±)-[(4aRS,5SR,8aSR)-5-(3-chloro-phenylethynyl)-5-hydroxy-octahydro-quinolin-1-yl]-(4-methyl-piperazin-1-yl)-methanone

LC-MS, M+1=416.2

EXAMPLE 10

(±)-(4aRS,5RS,8aSR)-5-(3-chloro-phenylethynyl)-5-hydroxy-octahydro-quinoline-1-carboxylic acid ethyl ester and (±)-(4aRS,5SR,8aSR)-5-(3-chloro-phenylethynyl)-5-hydroxy-octahydro-quinoline-1-carboxylic acid ethyl ester a) To a solution of trimethylsilylacetylene (1.54 ml, 10.8 mmol) in THF (10 ml), is added a solution of n-butyl-lithium in hexane (6.75 ml, 10.8 mmol; 1.6M in hexane) at 0° C. The reaction mixture is stirred at 0° C. for 45 minutes and then at room temperature for 20 hours. The reaction mixture is diluted with diethyl ether (100 ml), washed with saturated sodium bicarbonate solution (2×10 ml), dried over magnesium sulfate and concentrated in vacuo. Purification of the crude product (2.0 g) using silica gel chromatography (ethylacetate/hexane gradient 0-40% v/v) give (±)-(4aRS,5RS,8aSR)-5-hydroxy-5-trimethylsilanylethynyl-octahydro-quinoline-1-carboxylic acid ethyl ester. (1.48, 84%); 1H NMR (400 MHz; CDCl3): 1H NMR 0.1(s-overlap, 9H), 1.05 (t, 3H), 1.10-1.30 (m, 2H), 1.30-1.60 (m, 6H), 1.60-1.95 (m, 4H), 2.80-3.0 (m,1H), 3.25-3.50 (m, 1H), 3.50-3.65 (m, 1H), 3.95(m, 2H). Further chromatographic fractions all contain variable mixtures of (±)-(4aRS,5RS,8aSR)-5-hydroxy-5-trimethylsilanylethynyl-octahydro-quinoline-1-carboxylic acid ethyl ester and (±)-(4aRS,5SR,8aSR)-5-hydroxy-5-trimethylsilanylethynyl-octahydro-quinoline-1-carboxylic acid ethyl ester.

b) A mixture (approximately 5:1) of (±)-(4aRS,5RS,8aSR)-5-hydroxy-5-trimethylsilanylethynyl-octahydro-quinoline-1-carboxylic acid ethyl ester and (±)-(4aRS,5SR,8aSR)-5-hydroxy-5-trimethylsilanylethynyl-octahydro-quinoline-1-carboxylic acid ethyl ester (0.272 g, 0.84 mmol), 1-bromo-3-chloro-benzene (0.161 g, 0.84 mmol), copper(I)iodide (0.016 g, 0.093 mmol), triphenylphosphine (0.02 g,0.074 mmol), potassium carbonate (0.127 g, 0.92 mmol), palladium on carbon (10%) (10 mg) in dimethoxyethane (2 ml) and water (1 ml) are combined together and heated at 80° C. for 24 hours under argon atmosphere. The reaction mixture is cooled to room temperature, filtered through celite, washed with diethyl ether and concentrated in in vacuo to yield a crude oil. The crude oil (0.181 g) is purified using silica gel chromatography (ethylacetate/hexane gradient 0-30%) and fractions containing the desired compounds are collected and evaporated in vacuo to yield the first product (±)-(4aRS, 5RS,8aSR)-5-(3-chloro-phenylethynyl)-5-hydroxy-octahydro-quinoline-1-carboxylic acid ethyl ester. (140 mg, 46%). $^1$H NMR (400 MHz; CDCl3): 1.28 (t, 3H), 1.2 8-1.50 (m, 2H), 1.50-2.00 (m, 7H), 2.0-2.20 (m, 3H), 3.08 (m,1H), 3.55 (tm, 1H), 3.80 (m, 1H), 4.15 (q, 2H),7.24-7.40(m, 4H) and the second product (±)-(4aRS,5SR, 8aSR)-5-(3-chloro-phenylethynyl)-5-hydroxy-octahydro-quinoline-1-carboxylic acid ethyl ester (30 mg, 10%). $^1$H NMR (400 MHz; CDCl3): 1.29 (t, 3H), 1.41-1.58(m, 2H), 1.58-2.00(m, 8H), 2.08-2.18 (m, 2H), 3.16 (m,1H), 3.61 (m, 1H), 3.70 (m, 1H), 4.10 (m, 2H),7.16-7.30(m, 4H).

Following the same procedure the following compounds are obtained:

EXAMPLE 10a (±)-(4aRS,5SR,8aSR)-5-Hydroxy-5-m-tolylethynyl-octahydro-quinoline-1-carboxylic acid ethyl ester $^1$H NMR (400 MHz; CDCl3): 1.25 (t, 3H), 1.39-1.56 (m, 2H), 1.56-1.98 (m, 8H), 1.99-2.23 (m, 2H), 2.35 (s, 3H), 3.15 (m, 1H), 3.55-3.79 (m, 2H), 4.04-4.20 (m, 2H),7.10 (m, 1H)7.15-7.25 (m, 3H)

EXAMPLE 10b (±)-(4aRS,5RS,8aSR)-5-Hydroxy-5-m-tolylethynyl-octahydro-quinoline-1-carboxylic acid ethyl ester $^1$H NMR (400 MHz; CDCl3): 1.25 (t, 3H), 1.30-1.50 (m, 2H), 1.56-2.20 (m, 8H), 2.20-2.44 (m, 3H), 2.85-3.19(m, 1H), 3.54-3.63 (m, 1H), 3.69-3.84 (m, 1H), 4.07-4.19 (m, 2H),7.05-7.27 (m, 4H).

EXAMPLE 11

(±)-Ethyl-((1SR,3SR)-3-hydroxy-3-m-tolylethynyl-cyclopentyl)-carbamic acid methyl ester and (±)-ethyl-((1SR,3RS)-3-hydroxy-3-m-tolylethynyl-cyclopentyl)-carbamic acid methyl ester a) To a solution of 3-methoxy-cyclopent-2-enone (800 mg, 7.13 mmol) in 30 ml of an ethylamine solution in THF, (2.0 M, 60 mmol) acetic acid (200 µl) is added and the mixture stirred at 70° C. for 2 h. The reaction mixture is concentrated in vacuo and the residue is filtered through silica gel with acetone. The resulting solid is crystallized from dichloromethane/ether to yield 3-ethylamino-cyclopent-2-enone as white crystals, m.p. 136-136.5° C.

b) To a solution of 3-ethylamino-cyclopent-2-enone (500 mg, 4 mmol) in 4 ml THF and 1 ml DMF, sodium hydride (12 mmol) is added. After stirring the reaction mixture for 20 minutes at room temperature, methyl chloroformate (615 µl, 8 mmol) is added. After stirring for 15 minutes, the reaction mixture is quenched with saturated aqueous ammonium chloride solution and concentrated in vacuo. The residue is partitioned between brine and dichloromethane. The organic extracts are chromatographed on silica gel (30 g) with dichloromethane/methanol (95:5 v/v) as eluent to afford ethyl-(3-oxo-cyclopent-1-enyl)-carbamic acid methyl ester which is crystallized from dichloromethane/ether, m.p. 68-68.5° C.

c) Ethyl-(3-oxo-cyclopent-1-enyl)-carbamic acid methyl ester (400 mg, 2.18 mmol) is hydrogenated in methanol with Pd/C (10%, 80 mg) to yield (±)-ethyl-((R,S)-3-oxo-cyclopentyl)-carbamic acid methyl ester as a yellowish oil.

d) The reaction of (±)-ethyl-((R,S)-3-oxo-cyclopentyl)-carbamic acid methyl ester with lithium m-tolylacetylide is performed as in example 1. After chromatography on silicagel with hexane/acetone (5:1 v/v) as eluent, the title compound (±)-ethyl-((1SR,3RS)-3-hydroxy-3-m-tolyl-ethynyl-cyclopentyl)-carbamic acid methyl ester is first eluted [$R_f$=0.48 (TLC silica gel, hexane/ethyl acetate 1:1), HPLC-MS: 324.2 (M+Na)$^+$] followed by (±)-ethyl-((1SR, 3SR)-3-hydroxy-3-m-tolylethynyl-cyclopentyl)-carbamic acid methyl ester [$R_f$=0.39 (TLC silica gel, hexane/ethyl acetate 1:1), HPLC-MS: 324.2 (M+Na)$^+$], both as pale yellow oils.

What is claimed is:

1. A compound of formula I

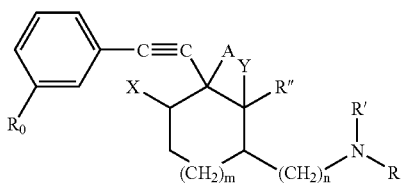

wherein
n is 0 or 1 and
A is hydroxy
X is hydrogen and
Y is hydrogen, or
A forms a single bond with X or with Y;
$R_0$ is hydrogen, ($C_{1-4}$)alkyl, ($C_{1-4}$)alkoxy, trifluoromethyl, halogen, cyano, nitro, —COOR$_1$ wherein R$_1$ is ($C_{1-4}$) alkyl or —COR$_2$ wherein R$_2$ is hydrogen or ($C_{1-4}$)alkyl, and
R is —COR$_3$, —COOR$_3$, —CONR$_4$R$_5$ or —SO$_2$R$_6$, wherein R$_3$ is ($C_{1-4}$)alkyl, ($C_{3-7}$)cycloalkyl or optionally substituted phenyl, 2-pyridyl or 2-thienyl, R$_4$ and R$_5$, independently, are hydrogen or ($C_{1-4}$)alkyl and R$_6$ is ($C_{1-4}$)alkyl, ($C_{3-7}$)cycloalkyl or optionally substituted phenyl,
R' is hydrogen or ($C_{1-4}$)alkyl and
R" is hydrogen, or ($C_{1-4}$)alkyl, or
R' and R" together form a group —CH$_2$—(CH$_2$)$_m$— wherein m is 0, 1 or 2, in which case one of n and m is different from 0,
with the proviso that R$_0$ is different from hydrogen, trifluoromethyl and methoxy when n is 0, A is hydroxy, X and Y are both hydrogen, R is COOEt and R' and R" together form a group —(CH$_2$)$_2$—,
in free base or acid addition salt form.

2. The compound of claim 1 which is (−)-(3aR,4S,7aR)-4-hydroxy-4-m-tolylethynyl-octahydroindole-1-carboxylic acid methyl ester in free base or acid addition salt form.

3. A process for the preparation of a compound of formula I, which comprises a) for the production of a compound of formula I wherein A is hydroxy, reacting a compound of formula II

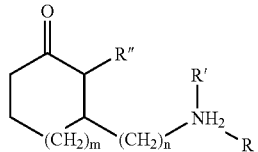

wherein m, n, R, R' and R" are as defined in claim 1, with a compound of formula III

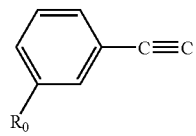

wherein R$_0$ is as defined in claim 1, or
b) for the production of a compound of formula I wherein A forms a single bond with X or with Y, dehydrating a compound of formula I wherein A is hydroxy, and
c) and recovering the resulting compound of formula I in free base or acid addition salt form.

4. A pharmaceutical composition comprising a compound of claim 1 in free base or pharmaceutically acceptable acid addition salt form, in association with a pharmaceutically acceptable carrier or diluent.

5. A method of treating traumatic and chronic degenerative processes of the nervous system, Parkinson's disease, senile dementia, Alzheimer's disease, Huntington's chorea, amyotrophic lateral sclerosis, multiple sclerosis, psychiatric diseases, schizophrenia, anxiety, depression, pain, itch, drug abuse, alcohol abuse disorder, nicotine abuse disorder, cocaine use disorder, epilepsy, cerebral ischemias, acute ischemias, ischemic diseases of the eye, muscle spasms, local spasticity, general spasticity or convulsions, which method comprises administering to a subject in need of such treatment a therapeutically effective amount of a compound of claim 1 in free base or pharmaceutically acceptable acid addition salt form.

6. A combination comprising a therapeutically effective amount of a compound of claim 1 in free base or pharmaceutically acceptable acid addition salt form and a second pharmaceutical agent, for simultaneous or sequential administration.

* * * * *

UNITED STATES PATENT AND TRADEMARK OFFICE
CERTIFICATE OF CORRECTION

PATENT NO. : 7,348,353 B2 Page 1 of 1
APPLICATION NO. : 10/497363
DATED : March 25, 2008
INVENTOR(S) : Gasparini et al.

It is certified that error appears in the above-identified patent and that said Letters Patent is hereby corrected as shown below:

Title Page,

Item [*] Notice: Subject to any disclaimer, the term of this patent is extended or adjusted under 35 USC 154(b) by 113 days Delete the phrase "by 113 days" and insert -- by 176 days --

Signed and Sealed this

Fourth Day of November, 2008

JON W. DUDAS
*Director of the United States Patent and Trademark Office*

UNITED STATES PATENT AND TRADEMARK OFFICE
CERTIFICATE OF CORRECTION

PATENT NO. : 7,348,353 B2
APPLICATION NO. : 10/497363
DATED : March 25, 2008
INVENTOR(S) : Fabrizio Gasparini et al.

Page 1 of 1

It is certified that error appears in the above-identified patent and that said Letters Patent is hereby corrected as shown below:

In the Claims

Col. 21 line 23 insert --m is 0 or 1--

Col. 21 delete lines 41 and 42 from claim 1 and insert --R' and R" together form a group –CH2-(CH2)p- wherein p is 0, 1 or 2, in which case one of n and p is different from 0--

Signed and Sealed this
Tenth Day of December, 2013

Margaret A. Focarino
*Commissioner for Patents of the United States Patent and Trademark Office*